United States Patent
Keller et al.

(10) Patent No.: US 10,725,137 B2
(45) Date of Patent: Jul. 28, 2020

(54) CALIBRATION OF MRI SYSTEMS USING PRE-DEFINED CONCENTRATIONS OF $^{19}$F ISOTOPES AS REFERENCE

(71) Applicant: B. BRAUN MELSUNGEN AG, Melsungen (DE)

(72) Inventors: Thorsten Keller, Neupotz (DE); Thore Dietrich, Berlin (DE); Eckart Fleck, Berlin (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 112 days.

(21) Appl. No.: 16/073,654

(22) PCT Filed: Feb. 1, 2017

(86) PCT No.: PCT/EP2017/052092
§ 371 (c)(1),
(2) Date: Jul. 27, 2018

(87) PCT Pub. No.: WO2017/134070
PCT Pub. Date: Aug. 10, 2017

(65) Prior Publication Data
US 2019/0041483 A1    Feb. 7, 2019

(30) Foreign Application Priority Data
Feb. 2, 2016    (EP) .................... 16153814

(51) Int. Cl.
*G01R 33/58*    (2006.01)
*G01R 33/56*    (2006.01)
(Continued)

(52) U.S. Cl.
CPC .............. *G01R 33/58* (2013.01); *A61K 49/06* (2013.01); *G01R 33/5601* (2013.01); *A61K 49/12* (2013.01); *A61K 49/18* (2013.01)

(58) Field of Classification Search
CPC .... G01R 33/58; G01R 33/5601; A61K 49/06; A61K 49/12; A61K 49/18; A61K 49/10
(Continued)

(56) References Cited

U.S. PATENT DOCUMENTS 5,227,727 A    7/1993    Segawa et al.
5,571,498 A *  11/1996   Cacheris ............ A61K 49/1806
                                                    424/9.365
(Continued)

FOREIGN PATENT DOCUMENTS

EP    2783703 A1    10/2014
JP    2010533182 A    10/2010
(Continued)

OTHER PUBLICATIONS

Liu, V.H., Vassiliou, C.C., Imaad, S.M. and Cima, M.J., 2014. Solid MRI contrast agents for long-term, quantitative in vivo oxygen sensing. Proceedings of the National Academy of Sciences, 111(18), pp. 6588-6593. (Year: 2014) (Year: 2014).*
(Continued)

*Primary Examiner* — Christopher P McAndrew

(57) ABSTRACT

A kit for calibrating a magnetic resonance imaging (MRI) system using defined concentration of $^{19}$F isotopes as well as a device for calibrating a MRI system using the kit. Further, a method for calibrating a MRI system employing the kit as well as to an entity comprising a defined concentration of $^{19}$F isotopes to be used in the calibration of a MRI system.

17 Claims, 1 Drawing Sheet

(51) Int. Cl.
*A61K 49/18* (2006.01)
*A61K 49/06* (2006.01)
*A61K 49/12* (2006.01)

(58) Field of Classification Search
USPC .......................................................... 324/308
See application file for complete search history.

(56) References Cited

U.S. PATENT DOCUMENTS

| | | | |
|---|---|---|---|
| 5,865,177 | A | 2/1999 | Segawa |
| 6,033,646 | A * | 3/2000 | Unger .................... A61K 9/127 264/4 |
| 6,071,494 | A * | 6/2000 | Unger .................... A61B 5/411 424/9.3 |
| 6,773,696 | B2 * | 8/2004 | Unger ................ A61K 49/0419 424/9.4 |
| 8,227,610 | B2 | 7/2012 | Janjic et al. |
| 8,400,151 | B2 | 3/2013 | Hulbert |
| 2006/0239919 | A1 * | 10/2006 | Wickline ........... A61K 49/1806 424/9.3 |
| 2008/0297151 | A1 | 12/2008 | Hirata et al. |
| 2009/0074673 | A1 * | 3/2009 | Janjic ................ A61K 49/1806 424/9.37 |
| 2009/0280055 | A1 * | 11/2009 | Schrader .............. A61K 31/025 424/1.11 |
| 2011/0110863 | A1 | 5/2011 | Ahrens et al. |
| 2011/0110867 | A1 | 5/2011 | Chung et al. |
| 2016/0228582 | A1 | 8/2016 | Dietrich et al. |

FOREIGN PATENT DOCUMENTS

| | | | |
|---|---|---|---|
| JP | 2015062693 | A | 4/2015 |
| KR | 20090132430 | A | 12/2009 |
| TW | 201545766 | A | 12/2015 |
| WO | 2011029910 | A1 | 3/2011 |
| WO | 2014154531 | A1 | 10/2014 |
| WO | 2015044312 | A1 | 4/2015 |

OTHER PUBLICATIONS

Wang, Yi-Xiang J., et al. "Efficacy and durability in direct labeling of mesenchymal stem cells using ultrasmall superparamagnetic iron oxide nanoparticles with organosilica, dextran, and PEG coatings." Materials 4.4 (2011): 703-715. (Year: 2011) (Year: 2011).*
Yee, G.G., Fulton, J.L. and Smith, R.D., 1992. Fourier transform infrared spectroscopy of molecular interactions of heptafluoro-1-butanol or 1-butanol in supercritical carbon dioxide and supercritical ethane. The Journal of Physical Chemistry, 96(15), pp. 6172-6181. (Year: 1992) (Year: 1992).*
Japanese Notice of Reasons for Rejection for Japanese Application No. 2018-557212, dated Jul. 23, 2019 with translation, 10 pages.
English Translation of the Korean Office Action for Korean Application No. 10-2018-7025282, dated Jul. 24, 2019, 9 pages.
International Search Report and Written Opinion for International Application No. PCT/EP2017/052092, dated Apr. 19, 2017—12 pages.
Pisani et al., "Perfluorooctyl Bromide Polymeric Capsules as Dual Contrast Agents for Ultrasonography and Magnetic Resonance Imaging", Advanced Functional Materials., 2008, vol. 18, pp. 2963-2971.
English Translation of the Chinese Office Action for Chinese Application No. 20178008800.X, dated Jan. 3, 2020, 13 pages.

* cited by examiner

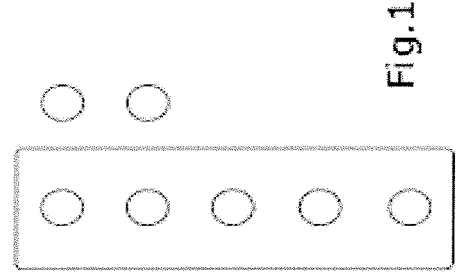
Fig.1
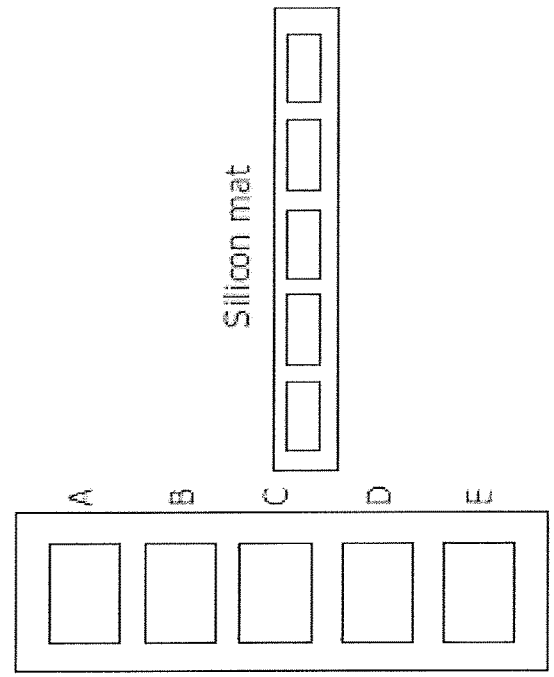
Fig.2
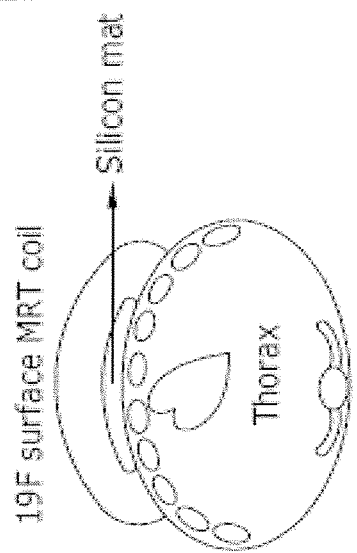

CALIBRATION OF MRI SYSTEMS USING PRE-DEFINED CONCENTRATIONS OF $^{19}$F ISOTOPES AS REFERENCE

CROSS REFERENCE TO RELATED APPLICATIONS

This application is the U.S. national phase application of PCT International Application No. PCT/EP2017/052092 filed Feb. 1, 2017, which claims priority to European Patent Application No. EP 16153814.5 filed Feb. 2, 2016, the contents of each application being incorporated by reference herein.

FIELD OF THE INVENTION

The present invention refers to a kit for calibrating a magnetic resonance imaging (MRI) system with reference to pre-defined concentrations of $^{19}$F isotopes as well as a device for calibrating a MRI system using the inventive kit. Further, the present invention relates to a method for calibrating a MRI system employing the inventive kit as well as to an entity comprising a defined concentration of $^{19}$F isotopes to be used in the calibration of a MRI system.

BACKGROUND OF THE INVENTION

Inflammatory diseases are by far the most important causes of morbidity and mortality worldwide. While there are effective diagnostic and therapeutic methods for acute inflammatory diseases (predominately caused by pathogens) in many cases, the diagnosis of chronic inflammatory diseases is mostly difficult, and the therapy thereof is limited to symptomatic measures. Non-invasive imaging methods, such as echocardiography, computer tomography and nuclear magnetic resonance spectroscopy, provide detailed anatomic information and are thus valuable tools for evaluating the function of organs. However, with none of the methods mentioned has it been possible to date to detect inflammatory processes unambiguously with high spatial resolution.

In recent years, the use of fluorinated compounds as contrast agents in the detection of inflammatory diseases has gained much attention in the medical field. Although first limited to $^{18}$F-labeled compounds such as $^{18}$F-labeled glucose, which can be detected via PET (Positron Emission Tomography), the current focus has shifted to $^{19}$F-containing compounds which can be detected via magnetic resonance imaging (MRI). As a further advantage, $^{19}$F-containing compounds are easier accessible and do not suffer from the drawback of being radioactive.

The detection of inflammatory processes in the (human) body by MRI is based on the phenomenon that fluorinated compounds, such as fluorocarbons, are taken up by monocytes/macrophages in such a way that the cells become specifically labeled. The fluorinated compound, also referred to as a contrast agent, thus accumulates in the inflamed tissue which is usually further comprising an increased concentration of macrophages at the inflamed site. A lot of attention has been focused on the development of suitable contrast agents that show a preference for the infected tissue while being well-tolerated by the patient.

DESCRIPTION OF THE RELATED ART

U.S. 2009/0280055 discloses the use of fluorocarbons such as perfluorooctyl bromide, perfluorooctane, perfluorodecalin or perfluoro-15-crown-5-ether for diagnostic purposes using MRI methods.

Another aspect which has been the subject of intensive studies in the field is the imaging method itself. Especially the provision of a homogenous magnetic field and improved quality of the obtained images has been the focus of intensive research.

U.S. Pat. No. 5,865,177 refers to a magnetic resonance imaging (MRI) diagnostic apparatus in which a radiofrequency (RF) pulse is applied from a RF coil to a biological body, and acquired nuclear magnetic resonance (NMR) signals therefrom are reconstructed so as to obtain an MRI image, the apparatus comprising a gantry for defining a space for MRI diagnosis, a RF shield, disposed inside the gantry and outside the RF and means for correcting a distribution of a RF magnetic field at the time of RF transmitting or receiving by the RF coil wherein the field correcting means is interposed between the biological body lying inside the shield and the RF coil.

U.S. 2008/0297151 discloses a magnetic resonance imaging (MRI) phantom for $^1$H/$^{19}$F signal detection that permits the stable and uniform dispersion of a vesicle and to accomplish the adjustment of a measured parameter for a $^1$H/$^{19}$F signal and performance confirmation by use of the phantom. The phantom has a gel comprising a vesicle comprising at least one of a perfluorocarbon and a superparamagnetic iron oxide particle.

WO 2011/029910 refers to a calibration phantom and method for the measuring and correcting of geometric distortions in an image of a body part of a patient. The calibration phantom comprises a plurality of separate detection elements arranged in a determined pattern, each detection element containing a product that is visible by the medical imaging system.

U.S. Pat. No. 8,400,151 provides a method for calibration of a magnetic resonance imaging system having a bore, a body coil mounted in the bore, a patient mat, a number of local coils mounted in the patient mat, an upconversion stage comprising a number of upconverters, and a processing stage.

U.S. Pat. No. 5,227,727 refers to method for regulating the radio frequency magnetic field distribution wherein a member containing a high molecular compound such as a molded sheet of non-conductive fiber or rubber, a PVA gel sheet or a PAR gel sheet is interposed between at least one transmitting coil and a receiving coil and a subject to be examined.

U.S. 2009/0074673 A1 discloses compositions and methods for producing cellular labels for tracking cells by MRI.

The state of the art so far focuses on providing a homogenous magnetic field in order to improve the resolution and quality of the obtained images. However, apart from being able to localize the inflamed tissue by way of MRI imaging, it is also desirable to gain information about the degree and severity of the inflammation itself, for example by quantitatively determining the amount of contrast agent which has been taken up by the macrophages. The imaging methods known today do not allow a quantification of the amount of contrast agent which has reached the targeted tissue by way of analyzing the obtained images. The present invention addresses inter alia said drawback.

DESCRIPTION OF THE INVENTION

It is therefore an object of the present invention to provide the means for quantitatively determining the degree of inflammation of a given inflammatory process by MRI imaging.

It was surprisingly found that the degree of inflammation could be determined by comparing the MRI signals obtained from inflamed tissue being treated with a $^{19}$F-containing contrast agent with signals stemming from one or more reference samples having defined concentrations of $^{19}$F isotopes. In the course of the invention, it was discovered that the amount of contrast agent present in the inflamed tissue corresponds to the strength of the obtained MRI signal which in turn can be put in relation to signals derived from defined concentrations of $^{19}$F isotopes. However, in order to obtain reliable and comparable data which allow an evaluation of the degree of inflammation, it is important to provide an accurate calibration curve for the MRI system used for the diagnostic methods.

Embodiments of the present invention are reflected in the independent claims. Preferred embodiments are reflected in the dependent claims.

A first embodiment of the invention is therefore a kit for calibrating a MRI (magnetic resonance imaging) system, said kit comprising two or more entities, wherein two or more of said entities have a defined concentration of $^{19}$F isotopes, and wherein two or more of said concentrations are different from each other.

In a preferred embodiment the concentration of the entities differ by at least 0.001 mmol-%, more preferably at least 0.01 mmol-%, especially 0.1 mmol-% based on the entity having the higher concentration.

It was surprisingly found that the amount of contrast agent accumulated in the inflamed tissue could be quantitatively determined through the employment of the inventive kit. The signals derived from the entities having defined concentrations of $^{19}$F isotopes serve as a means for calibrating the MRI system. The thus quantified signals can then be used as a reference to determine the concentration of $^{19}$F isotopes in the analyzed tissue which is believed to be directly linked to the activity of the macrophages which can usually be found in large numbers at the inflamed site.

Improved results were obtained in cases where sharply defined signals could be generated by avoiding any fluctuations in the magnetic field. Therefore, in a preferred embodiment, the defined concentration of $^{19}$F isotopes in each individual entity of the kit according to aspects of the invention is constant.

In order to obtain a reliable and accurate calibration curve of the MRI system, a variety of reference signals stemming from defined $^{19}$F isotope concentrations should be used. An embodiment of the present invention is therefore preferred wherein the number of entities in the kit is three or more, preferably five or more. This way an accurate and quantitative measurement can be provided which in turn allows a profound and substantiated diagnosis.

As discussed above, fluorinated contrast agents were found to be especially suited for the employment in MRI diagnosis of diseases related to inflammatory processes. In a preferred embodiment of the kit according to aspects of the invention, the $^{19}$F isotopes stem from a fluorinated contrast agent.

In diagnostic methods employing contrast agents, such as MRI imaging, it is especially important that the adverse effects and the stress caused by the diagnostic method are kept as minimal as possible. In particular, additional side effects due to intolerance of the contrast agent are to be avoided. Therefore, in a further preferred embodiment, the fluorinated contrast agent is selected from the group consisting of partially fluorinated carbon compounds, perfluorinated carbon compounds, linear, cyclic or polycyclic fluorinated alkanes, bis(perfluoroalkyl)alkanes, perfluoroethers, perfluoroamines, perfluoroalkyl bromide and perfluoroalkyl chloride. In a preferred aspect of the invention each entity of the kit comprises the same fluorinated contrast agent.

Especially, excellent results can be achieved with a kit wherein at least one entity, preferably all entities, comprise(s) a semifluorinated contrast agent, in particular a semifluorinated alkane.

In a particular preferred embodiment the fluorinated contrast agent is a semifluorinated compound of formula (I):

$$CF_3-(CF_2)_x-(CH_2)_y-CH_3 \qquad (I)$$

wherein x is an integer ranging from 1 to 8 and y is an integer ranging from 2 to 10.

It was surprisingly found that the adverse effects of the patient could be reduced while at the same time the uptake of the fluorinated contrast agent by the macrophages and its distribution in the blood stream was improved, when the fluorinated contrast agent was a semifluorinated compound of formula (I).

In an especially preferred embodiment of the kit according to aspects of the invention, the fluorinated contrast agent is perfluorohexyloctane (F6H8).

In order to generate a signal which can be detected the $^{19}$F isotopes should be able to exercise a certain degree of movement so that they can be excited by the magnetic field of the MRI system. Accordingly, an embodiment of the kit is preferred wherein the $^{19}$F isotopes possess a flexibility sufficient to generate a signal to be detected by a detector of an MRI system.

Apart from showing good compatibility and being medically inert (i.e. non-harmful when used in a medical setting), the source of the $^{19}$F isotopes should also allow a certain degree of flexibility of the isotopes. It was found that the best results with regard to signal accuracy were achieved when the contrast agent was in the form of a liquid. Therefore, an embodiment of the kit is preferred wherein the fluorinated contrast agent is present in the two or more entities in form of a liquid, preferably oil. An especially preferred fluorinated contrast agent is liquid at room temperature (25° C.).

A homogenous magnetic field is essential in obtaining accurate reference signals. In this regard, it was found that local distortions of the magnetic field can be avoided by homogenously distributing the fluorinated contrast agent within each entity of the kit according to aspects of the invention. Consequently, in a preferred embodiment the fluorinated contrast agent is homogenously distributed within each respective entity. Alternatively, the entity can be encapsulated. The fluorinated contrast agent is then homogenously distributed within the capsule.

Homogenously distributed for the purpose of the invention means that the contrast agent is evenly distributed within a given matrix material. Preferably, the local concentrations within one entity do not differ more than 0.01%, more preferably not more than 0.1%, in particular 1 to 1.5%.

It was surprisingly found that the best results with regard to signal quality and resolution could be achieved if the amount of fluorinated contrast agent in each entity was at least 10% by weight, preferably at least 20% by weight, based on the total weight of the respective entity. In a preferred embodiment the entity comprises the fluorinated contrast agent in an amount ranging from 15 to 95 wt.-%, more preferably from 20 wt.-% to 85 wt.-%, especially preferably from 25 to 75 wt.-%, in particular from 30 to 70 wt.-%, based on the total weight of the entity. If the amount is lower than 10% by weight, detecting the signal might prove difficult. If the amount is too high, there is a risk of oversaturation.

To provide easy handling of the entities containing the defined concentrations of $^{19}$F isotopes, the source of the $^{19}$F isotopes, for example the fluorinated contrast agent, may be embedded in a matrix material. An embodiment is therefore preferred wherein the two or more entities further comprise a matrix material.

Preferably, the fluorinated contrast agent is at least partially embedded in the matrix material of the two or more entities.

The matrix material is preferably selected from the group consisting of polysiloxane, polyolefin, silicon oil, mid chain triglycerides, polyorganosiloxane, gelatin, silicon rubber casting compound, silicon resin solution, two-component siloxane and two-component silicon and silicon with suitable catalysts.

Suitable catalysts may, for example, be selected from the group consisting of peroxides, ion catalysts, metal catalysts, in particular precious metal catalysts, and metal complex catalysts.

The matrix material is preferably selected from silicon containing compounds, especially selected from organosilicon compounds. Alternatively, the fluorinated contrast agents may be encapsulated in gelatin or packaged in plastic or glass.

The two or more entities comprised in the kit according to aspects of the invention may form an integral one-piece system, for example by being physically connected to each other.

Especially in diagnostics, each patient is different and requires different treatment. It is therefore desirable to be able to adjust the inventive kit according to the individual needs of each patient, for example by adapting the defined concentrations of $^{19}$F isotopes in order for the calibration to be as accurate as possible. Further, it would be desirable to be able to exchange one defined concentration of $^{19}$F isotopes for another without having to replace the whole kit. In a preferred embodiment, the kit according to aspects of the invention is therefore designed in a way that allows the two or more entities to be assembled and reassembled in a non-destructive way.

In a preferred embodiment, the two or more entities are in the form of tablets, capsules, tubes, dragees, cradle systems or pads. This way, the entities can be replaced and/or exchanged in a most convenient way.

In a preferred embodiment the two or more entities comprised in the kit according to aspects of the invention are located on one or more carrier(s). Preferably, the two or more entities are placed on the same carrier.

In a further preferred embodiment, the kit according to aspects of the invention is designed in a way that allows the two or more entities and the one or more carrier(s) to be assembled and dissembled in a non-destructive way.

The entities being placed on a carrier allow an easy handling of the inventive kit in calibration processes of MRI systems while at the same time allowing a high flexibility in adapting the kit to the individual requirements needed. However, care has to be taken to avoid inference of the carrier with the magnetic field and any undesirable side effects to the imaging procedure. Therefore, in a preferred embodiment of the kit according to aspects of the invention, the carrier is made out of an MRI inert material. A variety of materials may be employed, for example, glass, ceramics, plastic or metal, as long as the material itself does not interfere with the imaging process or causes artifacts in the obtained images.

In a preferred embodiment, the carrier is in the form of a pad and the two or more entities are in forms of tablets, preferably non-compressed tablets. However, other combinations of geometrical forms are also possible. In one preferred aspect of the invention the entity comprises a fluorinated contrast agent which is, preferably homogenously, distributed within a cured matrix material.

In the course of the present invention it was surprisingly found that especially high quality measurements can be obtained when the carrier has certain physical properties which not only ensure non-interference with the magnetic field but also increase the durability of the kit according to aspects of the invention, especially if the carrier is made out of a silicon-containing (Si-containing) material. In a preferred embodiment, the carrier has a Shore hardness, determined according to ISO 868, in the range of 15 to 55, preferably 20 to 50 and more preferably 25 to 45.

In a further preferred aspect the material of the carrier may have a density ranging from 0.25 to 1.75 g/cm$^3$, preferably 0.5 to 1.5 g/cm$^3$ and more preferably 0.9 to 1.25 g/cm$^3$, determined at 23° C. according to ISO 2781. Especially preferred the carrier material is a silicon containing material.

The physical dimensions of the kit according to aspects of the invention are mostly determined by the carrier which in turn should be sufficient to accommodate the two or more entities placed thereon. Advantageously, the entities are kept rather small to allow easy handling as well as high convenience for the patient who should be in close proximity to the kit to ensure high resolution images. In a preferred embodiment, the largest longitudinal extension of the two or more entities individually ranges from 2 to 50 mm, further preferably from 4 to 30 mm, especially 6 to 20 mm or 7 to 15 mm, particularly from 8 to 12 mm, for example 9 to 11 mm.

As discussed above, the kit according to aspects of the invention is to be employed in the calibration of MRI systems. A further subject of the present invention is therefore the use of a kit according to aspects of the invention as an external standard in MRI measurements. In particular, the MRI measurement is used for the diagnostic detection of inflammatory processes wherein the imaging process is based on measuring the nuclear magnetic resonance of $^{19}$F isotopes.

The kit according to aspects of the invention is especially useful in the detection of inflammatory processes such as inflammatory reactions peripheral to infarctions such as myocardial infarction and stroke; inflammation of organs, such as myocarditis, encephalitis, meningitis; multiple sclerosis; inflammation of the gastrointestinal tract, such as Crohn's disease; inflammation of the vessel, such as arteriosclerosis, in particular vulnerable plaques; detection of abscesses and arthritis.

The diagnostic detection is in particular based on non-invasive imaging procedure of the cardio-vascular system, including the myocardium, arteries and veins; inflammatory reactions occurring in disease processes like myocardial infarction, myocarditis, atherosclerosis and thrombosis leading to inflammatory and degenerative processes of the vasculature found in neurology such as stroke or tumor; pulmology such as thrombosis, inflammation, saccoidosis; gastroenterology such as tumor, inflammatory bowel diseases such as Crohn's disease; and rheumatology such as autoimmune disease of the vessels such as Takayasu arteritis.

A further subject of the present invention is a method for the production of a kit according to aspects of the invention comprising the following steps:

a) providing two or more entities, wherein two or more of said entities have a defined concentration of $^{19}$F isotopes, and wherein two or more of said concentrations are different from each other; and b) assembling the entities to obtain a kit.

In a preferred aspect of the method for the production of the kid the two or more of the entities are obtained by i) Providing a matrix material;

ii) Providing fluorinated contrast agent comprising $^{19}$F isotopes; and iii) Mixing the components of steps i) and ii).

In a preferred embodiment, the fluorinated contrast agent is liquid at room temperature (25° C.).

The matrix material in step i) is preferably selected from the group consisting of silicon containing compounds, organosilicon compounds, polysiloxane, polyolefin, silicon oil, mid chain triglycerides (MCT), polyorganosiloxane, gelatin, silicon rubber casting compound, silicon resin solution, two-component siloxane and two-component silicon. It was surprisingly found that a matrix material chosen from the above group does not hinder the flexibility of the $^{19}$F isotopes required to generate signals to be detected in the MRI measurement. As a further advantage, those materials do not pose any known risk to the human health or the natural environment.

In some embodiments it might be desirable for the kit to be solid. Therefore, in a preferred embodiment, the method according to aspects of the invention further comprises the step of curing the mixture of step iii). The curing can be carried out in any way known to the person skilled in the art, for example thermally or chemically. However, care should be taken that the curing conditions are compatible with the fluorinated contrast agent in order to avoid degradation of the same.

In some embodiments, it may be desirable for the mixture of step iii), i.e. the fluorinated contrast agent and the matrix material, to be liquid at room temperature. Therefore, in an alternative embodiment the method according to aspects of the invention further comprises the step of enclosing the mixture of step iii) in a capsule.

The shell of the capsule is made out of a MRI inert material, for a example a material containing gelatin.

As discussed above, an object of the present invention is the provision of means for quantitatively determining the degree of inflammation of a given inflammatory process by MRI imaging.

One means to the solution of said object is a device for the calibration of a MRI system employing a kit comprising two or more entities, wherein two or more of said entities have a defined concentration of $^{19}$F isotopes, said concentrations being different from each other.

Another subject of the invention is therefore a device for calibrating a MRI system comprising the following components:

i) detector coil for detecting the concentration of $^{19}$F isotopes in a tissue sample wherein the detector coil is part of an MRI system;

ii) kit comprising two or more entities, wherein two or more of said entities have a defined concentration of $^{19}$F isotopes, said concentrations being different from each other;

iii) tissue sample to be examined which has been treated with a $^{19}$F-fluorinated contrast agent;

wherein the kit and the tissue sample to be examined are both simultaneously present in the area to be scanned by the detection coil.

In order to avoid any disturbances during the imaging process which, for example, may be caused by movement or slipping of the kit and/or the tissue sample, the kit is preferably fixed in place with respect to the tissue sample. This can, for example, be done by attaching the kit to the tissue sample, or fixing both in close proximity to each other on a support system, such as a rack.

The device according to aspects of the invention is particularly suitable for imaging processes based on measuring the nuclear magnetic resonance of $^{19}$F isotopes. In those imaging processes the $^{19}$F isotopes are stimulated to generate a signal which is then detected by the detection coil. The accumulated data can then be used to generate a digital image of the scanned area.

The kit used in the inventive device is preferably a kit according to aspects of the invention.

A further means for achieving an object of the present invention is a method for the calibration of a MRI system with the help of reference signals generated by defined concentrations of $^{19}$F isotopes.

The method according to aspects of the invention for calibrating a MRI system comprises the following steps:

providing a kit comprising two or more entities, wherein two or more of said entities have a defined concentration of $^{19}$F isotopes, said concentrations being different from each other;

providing a sample tissue to be examined wherein the sample tissue has been treated with a $^{19}$F-fluorinated contrast agent (B) prior to examination;

providing a detection coil which is part of an MRI system;

placing the kit and the sample tissue in the area to be scanned by the detection coil;

simultaneously detecting the signals generated by the $^{19}$F isotopes in the kit and the sample tissue by the detection coil;

numerically evaluating the signals of the $^{19}$F isotopes of the kit conducting a calibration of the system based on the known concentration of the detected $^{19}$F isotopes of the kit.

The intensity of the signals generated by the $^{19}$F isotopes of the kit, corresponding to a certain concentration of $^{19}$F isotopes, are used as a reference for the signals generated by the $^{19}$F isotopes present in the examined tissue sample. Because of the defined concentration of the $^{19}$F isotopes in the kit, the intensity of said signals can be used as reference in determining the concentration of $^{19}$F isotopes in the examined tissue sample. The concentration of $^{19}$F isotopes in the tissue sample in turn serves as an indication of the degree of inflammation. Clinical studies showed an increased activity of macrophages in inflamed tissue. The fluorinated contrast agent containing $^{19}$F isotopes is believed to be phagocytized by the macrophages which thereby become specifically labeled. Therefore, it is believed that the higher the concentration of $^{19}$F isotopes in the tissue, the more severe the inflammation. The inventive method thus allows an estimation of the severity of inflammation by providing a way to quantitatively determine the concentration of $^{19}$F isotopes in inflamed tissue by comparison to reference signals corresponding to defined concentrations of $^{19}$F isotopes.

In light of the above, in a preferred embodiment, the method according to aspects of the invention further comprises the step of determining the concentration of $^{19}$F isotopes in the sample tissue by reference to the defined concentrations of $^{19}$F isotopes of the kit.

It has surprisingly and advantageously been found that the measurement can be conducted with the same offset-frequencies and at the same time with only one measurement. Methods known in the prior art require first a quantification of the contrast agent applied to the patient or a tissue and subsequent measurement by MRT.

Preferably, the offset frequencies used for the MCT measurement in the methods of the invention range from 6 to 14 Hz. For example for F6H8 an offset-frequency of 7.07 Hz is used.

In order to ensure accuracy of the calibration method as well as the system employed, a calibration of the system is preferable conducted with reference to each defined concentration of $^{19}F$ isotopes of the kit.

It was surprisingly found that the accuracy of the measurements can be improved if concentrations of the $^{19}F$ isotopes of the two or more entities are evaluated individually. Therefore, an embodiment is preferred wherein the signals caused by the different concentrations of $^{19}F$ isotopes in the different entities are individually evaluated.

The $^{19}F$ isotopes present in the kit and the sample tissue may stem from a variety of suitable compounds known in the state of the art. However, in a preferred embodiment the $^{19}F$ isotopes in the kit stem from a fluorinated contrast agent (A).

The $^{19}F$ isotopes present in the tissue sample stem from a fluorinated contrast agent (B).

The fluorinated contrast agents (A) and (B) are preferably individually selected from the group consisting of partially fluorinated carbon compounds, perfluorinated carbon compounds, linear, cyclic or polycyclic fluorinated alkanes, bis(perfluoroalkyl)alkanes, perfluoroethers, perfluoroamines, perfluoroalkyl bromide and perfluoroalkyl chloride.

The fluorinated contrast agent (A) and the fluorinated contrast agent (B) may be the same or different.

The concentration of fluorinated contrast agent (A) in each entity of the kit may be chosen in accordance with the individual requirements of each measurement. In any case, embodiments are preferred wherein the fluorinated contrast agent (A) is homogeneously distributed within each respective entity.

The tissue sample to be examined is treated with the fluorinated contrast agent (B) prior to examination. In the case where particular body parts or organs of a patient are to be examined, the fluorinated contrast agent (B) is administered to the patient prior to the examination and distributed in the blood stream of the patient. Depending on the nature of the fluorinated contrast agent (B) as well as the metabolism of the patient, a certain period of incubation might have to be considered to allow the fluorinated contrast agent (B) to reach the targeted tissue.

In a preferred embodiment the fluorinated contrast agent (B) is in the form of an emulsion, preferably an aqueous emulsion, comprising a fluorinated contrast agent, in particular a fluorinated contrast agent as described above, a medium-chain triglyceride (MCT) which is miscible with the fluorinated contrast agent at 20° C. and an emulsifier. Suitable emulsions are for example described in patent applications WO 2015/044312 and EP 2783703.

Especially preferred is an aqueous emulsion comprising a semifluorinated compound of formula (I), such as F6H8, and a medium chain triglyceride (MCT) which is miscible with fluorinated compound at 20° C.

In an especially preferred embodiment, the kit employed in the method according to aspects of the invention is a kit according to aspects of the invention.

A further preferred embodiment is the use of method according to aspects of the invention in the diagnostic detection with an imaging procedure wherein the imaging process is based on measuring the nuclear magnetic resonance of the $^{19}F$ isotopes.

A further means for solving an object of the present invention is an entity comprising a defined concentration of $^{19}F$ isotopes which can be employed in the calibration of MRI systems.

A further subject is therefore an entity comprising a defined concentration of a $^{19}F$ isotopes-containing contrast agent and a matrix material wherein the contrast agent is at least partially embedded and/or encapsulated by the matrix material.

The entity is particularly suitable to be employed in a kit according to aspects of the invention or a device according to aspects of the invention or a method for calibrating an MRI system according to aspects of the invention.

The $^{19}F$ isotopes comprised in the inventive entity preferably possess sufficient flexibility to generate a signal to be detected by a detector of an MRI system. The matrix material should therefore be chosen accordingly.

Preferably the matrix material is selected from the group consisting of silicon oil, digestible polymers, polyolefins, polysiloxanes, polyorganosiloxane, silicon rubber casting compound, silicon resin solution, two-component siloxane and two-component silicone. Preferably the digestible polymer is chosen from the group consisting of gelatin and mid-chain triglycerides (MCT). It was found that those materials do not hinder the movement of the $^{19}F$ isotopes and thus allow for required flexibility to be detectable in MRI measurements.

It was surprisingly found that the $^{19}F$ isotopes can be especially well detected if the matrix material is in the form of an oil, preferably a silicon oil.

In a preferred embodiment the fluorinated contrast agent is dissolved in the silicon oil. Preferably the fluorinated contrast agent is selected from the group consisting of partially fluorinated carbon compounds, perfluorinated carbon compounds, linear, cyclic or polycyclic fluorinated alkanes, bis(perfluoroalkyl)alkanes, perfluoroethers, perfluoroamines, perfluoroalkyl bromide and perfluoroalkyl chloride.

In an especially preferred embodiment the fluorinated contrast agent is a semifluorinated compound of formula (I):

$$CF_3-(CF_2)_x-(CH_2)_y-CH_3 \tag{I}$$

wherein x is an integer ranging from 1 to 8 and y is an integer ranging from 2 to 10.

In a particular preferred embodiment, the fluorinated contrast agent is perfluorohexyloctane (F6H8).

The entity according to aspects of the invention may either be used in a kit, in particular a kit according to aspects of the invention, or separately, for example as a replacement. Further, if the entity is used as part of the kit according to aspects of the invention, more than one entity having different concentrations of $^{19}F$ isotopes may be individually assembled in accordance with the requirements of each individual case.

A further subject is therefore the use of an entity according to aspects of the invention in a kit according to aspects of the invention or in a device according to aspects of the invention or in a method according to aspects of the invention.

The invention is explained in more detail with reference to the examples given below. However, it should be clear that the examples are not to be understood as limiting the spirit of the invention.

The following examples were prepared using F6H8 (Fluoron GmbH, Germany) as the source of $^{19}$F isotopes and SF00 2k-Silikon (Silikonfabrik, Deutschland), a two-component silicon derived from a set consisting of a base material and a catalyst. The amount of each component is given in table 1.

TABLE 1

| | | Amount [g] | | | |
| | | SF00 2k-Silikon | | | |
| Example | F6H8 conc. [w/w] | base material | catalyst | F6H8 | Volume [μl] F6H8 |
| --- | --- | --- | --- | --- | --- |
| 1 | 1.0 | 4.32 | 4.32 | 0.09 | 65.6 |
| 2 | 2.5 | 2.18 | 2.18 | 0.11 | 84.2 |
| 3 | 4.0 | 2.01 | 2.01 | 0.16 | 126.4 |
| 4 | 5.5 | 1.86 | 1.86 | 0.21 | 162.4 |
| 5 | 7.0 | 2.30 | 2.30 | 0.35 | 260.2 |

In a first step, the two components of the silicon, the base material and the catalyst, were weight into a snap-on lid tube and stirred at 1000 rpm using a magnetic stirrer. Meanwhile, the amount of F6H8 needed to reach the respective concentration was added with the help of a pipette. Afterwards, the mixture was transferred to a 1.5 ml test tube and centrifuged at 13000 rpm and 20° C. until the mixture was cured.

BRIEF DESCRIPTION OF THE DRAWINGS

The invention is best understood when read in connection with the accompanying drawings.

FIG. 1 shows the inventive kit as well as the inventive entities in the exemplary form of a pad and tablets, respectively.

FIG. 2 shows the schematic assembly of the inventive kit in the form of a pad in relation to a patient and a MRI system, the abbreviation A, B, C, D and E illustrating the single entities of the pad with differnt concentrations of $^{19}$F isotopes.

The invention claimed is:

1. A kit for calibrating a magnetic resonance imaging (MRI) system, said kit comprising a plurality of entities, wherein two or more of said plurality of entities have a defined concentration of $^{19}$F isotopes and a matrix material, wherein the $^{19}$F isotopes stem from a contrast agent which is at least partially embedded and/or encapsulated by the matrix material, and wherein two or more of said concentrations are different from each other, and wherein the $^{19}$F isotopes stem from a fluorinated contrast agent selected from a semifluorinated compound of formula (I):

$$CF_3-(CF_2)_x-(CH_2)_y-CH_3 \qquad (I)$$

wherein x is an integer ranging from 1 to 8 and y is an integer ranging from 2 to 10.

2. The kit according to claim 1, wherein the fluorinated contrast agent is present in the two or more entities in a form of a liquid.

3. The kit according to claim 1, wherein the amount of fluorinated contrast agent in at least one entity is at least 10% by weight based on the total weight of the at least one entity.

4. The kit according to claim 1, wherein the matrix is selected from silicon containing compounds, especially selected from organosilicon compounds.

5. The kit according to claim 1, wherein the matrix is selected from organosilicon compounds.

6. Use of the kit according to claim 1 as an external standard in MRI measurements.

7. A method for producing a kit, the method comprising the following steps:
a) providing a plurality of entities, wherein two or more of said plurality of entities have a defined concentration of $^{19}$F isotopes and a matrix material, wherein the $^{19}$F isotopes stem from a contrast agent which is at least partially embedded and/or encapsulated by the matrix material, and wherein two or more of said concentrations are different from each other, and wherein the $^{19}$F isotopes stem from a fluorinated contrast agent selected from a group consisting of partially fluorinated carbon compounds, perfluoroalkyl bromide and perfluoroalkyl chloride semifluorinated compound of formula (I):

$$CF_3-(CF_2)_x-(CH_2)_y-CH_3 \qquad (I)$$

wherein x is an integer ranging from 1 to 8 and y is an integer ranging from 2 to 10; and
b) assembling the entities to obtain the kit.

8. The method according to claim 7, wherein two or more of the plurality of entities are obtained by:
i) providing a matrix material;
ii) providing the fluorinated contrast agent comprising $^{19}$F isotopes; and
iii) mixing the components of steps i) and ii).

9. The method according to claim 8, further comprising the step of curing the mixture of step iii).

10. The method according to claim 8, further comprising the step of enclosing the mixture of step iii) in a capsule.

11. A device for calibrating a MRI system comprising the following components:
i) a detector coil for detecting a concentration of $^{19}$F isotopes in a tissue sample, wherein the detector coil is part of an MRI system;
ii) a kit comprising a plurality of entities, wherein two or more of said plurality of entities each have a defined concentration of $^{19}$F isotopes, and a matrix material, wherein the $^{19}$F isotopes stem from a contrast agent which is at least partially embedded and/or encapsulated by the matrix material, said concentrations being different from each other, and wherein the $^{19}$F isotopes stem from a fluorinated contrast agent selected from a semifluorinated compound of formula (I):

$$CF_3-(CF_2)_x-(CH_2)_y-CH_3 \qquad (I)$$

wherein x is an integer ranging from 1 to 8 and y is an integer ranging from 2 to 10;
iii) tissue sample to be examined which has been treated with a $^{19}$F-fluorinated contrast agent;
wherein the kit and the tissue sample to be examined are both simultaneously present in an area to be scanned by the detector coil.

12. The device according to claim 11 wherein the kit is fixed in place with respect to the tissue sample.

13. A method for calibrating a MRI system comprising the following steps:
providing a kit comprising two or more entities, wherein each of said two or more entities have a defined concentration of $^{19}$F isotopes, and a matrix material wherein the $^{19}$F isotopes stem from a contrast agent which is at least partially embedded and/or encapsulated by the matrix material, said defined concentrations being different from each other, wherein the $^{19}$F isotopes stem from a fluorinated contrast agent selected from a semifluorinated compound of formula (I):

$$CF_3-(CF_2)_x-(CH_2)_y-CH_3 \qquad (I)$$

wherein x is an integer ranging from 1 to 8 and y is an integer ranging from 2 to 10;

providing a sample tissue to be examined wherein the sample tissue has been treated with a $^{19}$F-fluorinated contrast agent prior to examination;

providing a detection coil which is part of an MRI system;

placing the kit and the sample tissue in an area to be scanned by the detection coil;

simultaneously detecting signals generated by the $^{19}$F isotopes in the kit and the sample tissue by the detection coil;

numerically evaluating the signals of the $^{19}$F isotopes of the kit; and calibrating the system based on the known concentration of the detected 19F isotopes of the kit.

14. The method according to claim 13, wherein a calibration of the system is conducted with reference to each defined concentration of $^{19}$F isotopes of the kit.

15. The method according to claim 13, further comprising the step of:

determining the concentration of $^{19}$F isotopes in the sample tissue by reference to the defined concentrations of $^{19}$F isotopes of the kit.

16. The method according to claim 13, wherein the fluorinated contrast agent is in the form of an aqueous emulsion comprising a semifluorinated compound and a medium chain triglyceride (MCT) which is miscible with the semifluorinated compound at 20° C.

17. An entity comprising a defined concentration of a $^{19}$F-containing contrast agent and a matrix material wherein the contrast agent is at least partially embedded and/or encapsulated by the matrix material and wherein the $^{19}$F isotopes stem from a fluorinated contrast agent selected from a semifluorinated compound of formula (I):

$$CF_3-(CF_2)_x-(CH_2)_y-CH_3 \qquad (I)$$

wherein x is an integer ranging from 1 to 8 and y is an integer ranging from 2 to 10.

* * * * *